United States Patent
Moore et al.

(10) Patent No.: US 9,434,678 B2
(45) Date of Patent: Sep. 6, 2016

(54) PROCESS FOR PREPARING ALKYL PYROGLUTAMIC ACIDS

(71) Applicant: ANGUS Chemical Company, Buffalo Grove, IL (US)

(72) Inventors: David Wayne Moore, Hebron, IL (US); Douglas John Bugajsky, Bolingbrook, IL (US)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 0 days.

(21) Appl. No.: 14/653,542

(22) PCT Filed: Dec. 20, 2013

(86) PCT No.: PCT/US2013/076930
§ 371 (c)(1),
(2) Date: Jun. 18, 2015

(87) PCT Pub. No.: WO2014/100591
PCT Pub. Date: Jun. 26, 2014

(65) Prior Publication Data
US 2016/0194271 A1    Jul. 7, 2016

Related U.S. Application Data

(60) Provisional application No. 61/740,063, filed on Dec. 20, 2012.

(51) Int. Cl.
C07C 209/34 (2006.01)
C07C 213/02 (2006.01)

(52) U.S. Cl.
CPC .......... *C07C 209/34* (2013.01); *C07C 213/02* (2013.01)

(58) Field of Classification Search
CPC .................................................. C07C 217/42
See application file for complete search history.

(56) References Cited

U.S. PATENT DOCUMENTS

2011/0224460 A1    9/2011   Moore
2012/0196963 A1    8/2012   Swedo

OTHER PUBLICATIONS

International Preliminary Report on Patentability for PCT/US2013/076930, mailed Jun. 23, 2015.
International Search Report and Written Opinion for PCT/US2013/076930, mailed Mar. 24, 2014.

*Primary Examiner* — Clinton Brooks
(74) *Attorney, Agent, or Firm* — Foley & Lardner LLP

(57) ABSTRACT

This disclosure relates to methods for limiting the undesired reverse Mannich reaction during the hydrogenation reduction of one or more nitro functional groups (—$NO_2$) to their corresponding amines (—$NH_2$).

20 Claims, No Drawings

PROCESS FOR PREPARING ALKYL PYROGLUTAMIC ACIDS

CROSS-REFERENCE TO RELATED APPLICATIONS

This applications is a 371 National Phase Application of PCT/US2013/076930, filed Dec. 20, 2013, which claims benefit of U.S. Provisional Application Ser. No. 61/740,063, filed Dec. 20, 2012, the disclosures of which are incorporated herein by reference in their entireties.

BACKGROUND OF THE INVENTION

1. Field of the Invention

This disclosure relates to methods for limiting the undesired reverse Mannich reaction during the hydrogenation reduction of one or more nitro functional groups (—$NO_2$) to their corresponding amines (—$NH_2$).

2. Description of Related Art

The production of zero VOC (volatile organic compound) paint neutralizers requires hydrogenation of one or more nitro functional groups (—$NO_2$) to their corresponding amines (—$NH_2$). However, this hydrogenation also results in the production of undesired byproducts via a reverse Mannich reaction. This limits the utility of the zero VOC paint neutralizers. To qualify a material for global use in a zero VOC paint applications, the end product must be substantially free of the undesired byproducts.

SUMMARY OF THE INVENTION

In a broad aspect, the disclosure provides a hydrogenation process where a reverse Mannich reaction, which gives the undesired byproducts, is minimized. In particular, the disclosure provides methods for limiting the undesired reverse Mannich reaction during the reduction of one or more nitro functional groups (—$NO_2$) to their corresponding amines (—$NH_2$). Such methods are especially useful in method of producing zero VOC (volatile organic compound) paint neutralizers.

Thus, one aspect of the disclosure (embodiment 1) provides a method of producing a compound of formula (I):

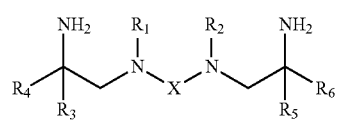

(I)

wherein
$R^1$, $R^2$, $R^3$, $R^4$, $R^5$, and $R^6$ are independently selected from H, $C_1$-$C_6$ alkyl, $C_3$-$C_8$ cycloalkyl, $C_3$-$C_8$ cycloalkyl($C_1$-$C_6$ alkyl), aryl, aryl($C_1$-$C_6$ alkyl), heteroaryl, and heteroaryl ($C_1$-$C_6$ alkyl); and
X is selected from $C_2$-$C_{20}$ alkylene, $C_2$-$C_{20}$ heteroalkylene, $C_2$-$C_{20}$ alkenylene, $C_2$-$C_{20}$ alkynylene, $C_3$-$C_8$ cycloalkyl, aryl, and —Y—Z—Y—;
wherein each Y independently is $C_1$-$C_{10}$ alkylene, or $C_2$-$C_{10}$ heteroalkylene, and Z is aryl, heteroaryl, or heterocyclyl;
the method comprising reacting a compound of formula (II):

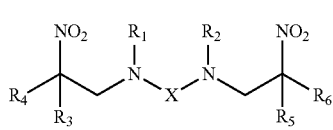

(II)

wherein $R^1$, $R^2$, $R^3$, $R^4$, $R^5$, $R^6$, and X are as defined above;
with $H_2$ in a solvent and in the presence of: a) a catalyst, b) at least about 0.1 molar equivalents of a nitro($C_1$-$C_{10}$ alkane) optionally substituted with one or more OH groups, and c) at least about 0.1 molar equivalents of formaldehyde.

Another aspect of the disclosure (embodiment 2) provides a method for producing a compound of formula:

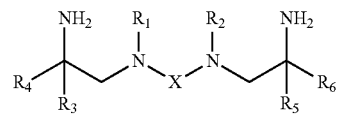

wherein
$R^1$, $R^2$, $R^3$, $R^4$, $R^5$, and $R^6$ are independently selected from H, $C_1$-$C_6$ alkyl, $C_3$-$C_8$ cycloalkyl, $C_3$-$C_8$ cycloalkyl($C_1$-$C_6$ alkyl), aryl, aryl($C_1$-$C_6$ alkyl), heteroaryl, and heteroaryl ($C_1$-$C_6$ alkyl); and
X is selected from $C_2$-$C_{20}$ alkylene, $C_2$-$C_{20}$ heteroalkylene, $C_2$-$C_{20}$ alkenylene, $C_2$-$C_{20}$ alkynylene, $C_3$-$C_8$ cycloalkyl, aryl, and —Y—Z—Y—;
wherein each Y independently is $C_1$-$C_{10}$ alkylene, or $C_2$-$C_{10}$ heteroalkylene, and Z is aryl, heteroaryl, or heterocyclyl;
the method comprising reacting a compound of formula:

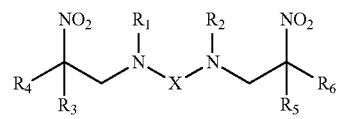

wherein $R^1$, $R^2$, $R^3$, $R^4$, $R^5$, $R^6$, and X are as defined above;
with hydrogen gas in the presence of a catalyst,
the improvement comprising conducting the reaction in the presence of a) at least about 0.1 molar equivalents of a nitro($C_1$-$C_{10}$ alkane) optionally substituted with one or more OH groups, and b) at least about 0.1 molar equivalents of formaldehyde.

DETAILED DESCRIPTION OF THE INVENTION

In embodiment 3, the disclosure provides methods of embodiment 1 or 2 wherein reacting is optionally in the presence of d) from about 0.0005 to about 0.2 molar equivalents of triethylamine. Embodiment 4 provides methods of embodiment 3, wherein from about 0.005 to about 0.05 molar equivalents of triethylamine is used. Embodiment 5 provides methods of any one of embodiments 3 and 4, wherein from about 0.01 to about 0.04 molar equivalents of triethylamine is used. In embodiment 6, the disclosure provides methods of any one of embodiments 3-5, wherein from about 0.01 to about 0.03 molar equivalents of triethylamine is used. In embodiment 7, the disclosure provides methods of any one of embodiments 3-6, wherein from about 0.025 of triethylamine is used. In embodiment 8, the disclosure provides methods of any one of embodiments 3-7, wherein another basic amine can be used instead of triethylamine. Examples of other suitable basic amines include, but are not limited to, tri($C_1$-$C_6$ alkyl)amine, tri (hydroxy $C_1$-$C_6$ alkyl)amine, quinuclidine, morpholine, piperidine, pyridine, imidazole, or alkylimidazole.

In embodiment 9, the disclosure provides method of any one of embodiments 1-8, wherein the catalyst is a nickel- or platinum-based catalyst. In embodiment 10, the disclosure provides methods of embodiment 9, wherein the catalyst is nickel-based catalyst. In embodiment 11, the catalyst of embodiment 10 is Raney nickel (Ra/Ni) catalyst. In embodiment 12, the disclosure provides methods of embodiment 9, wherein the catalyst is platinum-based catalyst. In embodiment 13, the catalyst of embodiment 12 is $PtO_2$ catalyst.

In embodiment 14, the disclosure provides method of any one of embodiments 1-13, wherein the nitro($C_1$-$C_{10}$ alkane) is 2-nitropropane, 2-methyl-2-nitro-1-propanol, or 2-methyl-2-nitro-1,3-propanediol. Embodiment 15 provides methods of embodiment 14, wherein nitro($C_1$-$C_{10}$ alkane) is 2-nitropropane. Embodiment 16 provides methods of embodiment 14, wherein nitro($C_1$-$C_{10}$ alkane) is 2-methyl-2-nitro-1-propanol. Embodiment 17 provides methods of embodiment 14, wherein nitro($C_1$-$C_{10}$ alkane) is 2-methyl-2-nitro-1,3-propanediol.

In embodiment 18, the disclosure provides method of any one of embodiments 1-17, wherein nitro($C_1$-$C_{10}$ alkane) is present in about 0.1 to about 2 molar equivalent. Embodiment 19 provides methods of embodiment 18, wherein nitro($C_1$-$C_{10}$ alkane) is present in about 0.1 to about 1 molar equivalents. Embodiment 20 provides methods of embodiment 18, wherein nitro($C_1$-$C_{10}$ alkane) is present in about 0.2 to about 0.8 molar equivalents. Embodiment 21 provides methods of embodiment 18, wherein nitro($C_1$-$C_{10}$ alkane) is present in about 0.4 to about 0.6 molar equivalents. Embodiment 22 provides methods of embodiment 18, wherein nitro($C_1$-$C_{10}$ alkane) is present in about 0.5 molar equivalents. Embodiment 23 provides methods of embodiment 18, wherein nitro($C_1$-$C_{10}$ alkane) is present in about 0.25 molar equivalents.

In embodiment 24, the disclosure provides method of any one of embodiments 1-23, wherein formaldehyde is present in about 0.05 to about 2 molar equivalent. Embodiment 25 provides methods of embodiment 24, wherein formaldehyde is present in about 0.1 to about 1 molar equivalents. Embodiment 26 provides methods of embodiment 24, wherein formaldehyde is present in about 0.2 to about 0.8 molar equivalents. Embodiment 27 provides methods of embodiment 24, wherein formaldehyde is present in about 0.4 to about 0.6 molar equivalents. Embodiment 28 provides methods of embodiment 24, wherein formaldehyde is present in about 0.5 molar equivalents. Embodiment 29 provides methods of embodiment 24, wherein formaldehyde is present in about 0.25 molar equivalents.

Solvents suitable for use in the methods of the disclosure include, but are not limited to, alcohols, glycols, organic protic solvents, organic aprotic solvents, or mixture thereof. Examples include methanol, ethanol, n-propanol, isopropanol, other lower alcohols, diethyl ether, THF, 1,4-dioxane, ethyl acetate, acetone, toluene, benzene, pentane, cyclopentane, hexane, cyclohexane, or any combination thereof. In embodiment 30, the disclosure provides method of any one of embodiments 1-29, wherein the solvent is selected from methanol, ethanol, n-propanol, isopropanol, diethyl ether, THF, 1,4-dioxane, toluene, benzene, and any combination thereof. In embodiment 31, the disclosure provides method of any one of embodiments 1-29, wherein the solvent is selected from methanol, ethanol, n-propanol, isopropanol, and any combination thereof. In embodiment 32, the disclosure provides method of any one of embodiments 1-29, wherein the solvent is methanol.

Embodiment 33 provides methods according to any one of embodiment 1-32, wherein $R^1$, $R^2$, $R^3$, $R^4$, $R^5$, and $R^6$ are independently selected from H and $C_1$-$C_6$ alkyl. In embodiment 34, the methods of embodiment 33 are where $R^3$, $R^4$, $R^5$, and $R^6$ are independently selected from $C_1$-$C_6$ alkyl.

Embodiment 35 provides methods of embodiment 35, wherein $R^3$, $R^4$, $R^5$, and $R^6$ are each methyl.

Embodiment 36 provides methods according to any one of embodiment 1-32, wherein $R^1$ and $R^2$ are independently selected from H. Embodiment 37 provides methods of embodiment 36, wherein $R^3$, $R^4$, $R^5$, and $R^6$ are independently selected from H and $C_1$-$C_6$ alkyl. In embodiment 38, the methods of embodiment 36 are where $R^3$, $R^4$, $R^5$, and $R^6$ are independently selected from $C_1$-$C_6$ alkyl, In embodiment 39, the methods of embodiment 38 are where $R^3$, $R^4$, $R^5$, and $R^6$ are each methyl Embodiment 40 provides methods according to any one of embodiment 1-39, wherein X is $C_2$-$C_{20}$ alkylene or $C_2$-$C_{20}$ heteroalkylene.

Embodiment 41 provides composition according to any one of embodiments 1-40 where X is $C_2$-$C_{20}$ alkylene. In embodiment 42, X is hexylene.

Embodiment 43 provides composition according to any one of embodiments 1-40 where X is —$(CH_2)_2$—O—$(CH_2)_2$—O—$(CH_2)_2$—.

Embodiment 44 provides methods according to any one of embodiment 1-40, wherein X is $C_2$-$C_{20}$ heteroalkylene, which is a polyoxyalkylene moiety having two or more oxyalkyl groups that are the same or different. In embodiment 45, heteroalkylene is polyethylene glycol, polypropylene glycol, polytetramethylene glycol, or a combination thereof. In embodiment 46, heteroalkylene is polyethylene glycol, polypropylene glycol, or a combination thereof. Embodiment 47 provides composition according to any preceding embodiments where heteroalkylene is polyethylene glycol. In embodiment 48, the disclosure provides compositions of any one of embodiments 44-47 wherein polyoxyalkylene moiety (e.g., polyethylene glycol) has a molecular weight between about 100 and about 2000. In embodiment 49, the molecular weight is between about 100 and about 1000. In embodiment 50, the molecular weight is between about 200 and about 1000.

Compounds that can be prepared by the methods (i.e., compounds of formula (I)) of the disclosure include (embodiment 51):

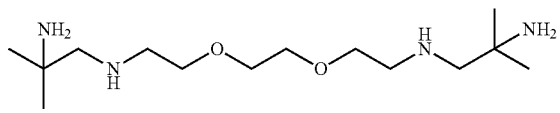 [SMILES: CC(C)(N)CNCCOCCOCCNCC(C)(C)N]

$N^1$,$N^{1'}$-(2,2'-(ethane-1,2-diylbis(oxy))bis(ethane-2,1-diyl))bis(2-methylpropane-1,2-diamine), or

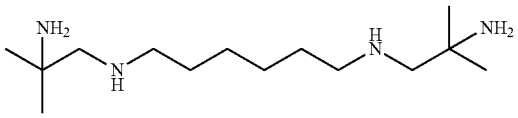 [SMILES: CC(C)(N)CNCCCCCCNCC(C)(C)N]

$N^1$,$N^{1'}$-(hexane-1,6-diyl)bis(2-methylpropane-1,2-diamine).

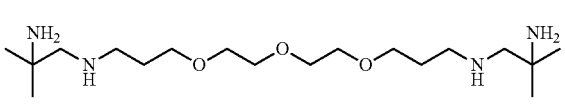 [SMILES: CC(C)(N)CNCCCOCCOCCOCCCNCC(C)(C)N]

$N^1$,$N^{1'}$-(3,3'-(2,2'-oxybis(ethane-2,1-diyl)bis(oxy))bis(propane-3,1-diyl))bis(2-methylpropane-1,2-diamine)

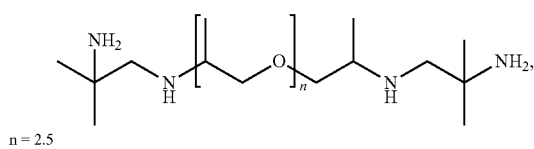

n = 2.5

$N^1,N^{1'}$-(Jeffamine® D-230)bis(2-methylpropane-1,2-diamine)

In embodiment 52, the disclosure provides method of any one of embodiments 1-32, wherein the compound of formula (I) is:

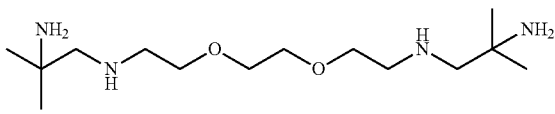 [SMILES: CC(C)(N)CNCCOCCOCCNCC(C)(C)N]

$N^1,N^{1'}$-(2,2'-(ethane-1,2-diylbis(oxy))bis(ethane-2,1-diyl)) bis(2-methylpropane-1,2-diamine), or

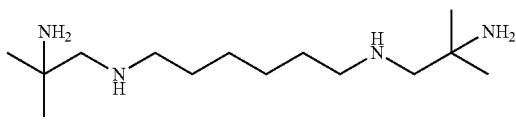 [SMILES: CC(C)(N)CNCCCCCCNCC(C)(C)N]

$N^1,N^{1'}$-(hexane-1,6-diyl)bis(2-methylpropane-1,2-diamine).

In embodiment 53, the disclosure provides method of any one of embodiments 1-52, wherein reacting the compounds of formula (II) is at temperature between about 30 to about 100° C. In embodiment 54, temperature is between about 40 to about 80° C. In embodiment 55, temperature is about 50 to about 70° C. In embodiment 48, temperature is about 50° C. In embodiment 56, temperature is about 65° C.

In embodiment 57, the disclosure provides method of any one of embodiments 1-56, wherein reacting the compounds of formula (II) is at pressure of about 100 psi to about 1500 psi. In embodiment 58, the pressure is between about 300 psi to about 1000 psi. In embodiment 59, the pressure is between about 500 psi to about 1000 psi. In embodiment 60, the pressure is between about 600 psi to about 800 psi. In embodiment 61, the pressure is about 600 psi. In embodiment 62, the pressure is about 700 psi. In embodiment 63, the pressure is about 750 psi. In embodiment 64, the pressure is about 800 psi.

DEFINITIONS

The following terms and expressions used have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. "===" means a single or double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 20 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl, and 2-propyl-2-heptenyl. The term "alkenylene" refers to a divalent alkenyl group, where alkenyl is as defined herein.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 20 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. The term "alkylene" refers to a divalent alkyl group, where alkyl is as defined herein.

The term "alkynyl" as used herein, means a straight or branched chain hydrocarbon group containing from 2 to 10 carbon atoms unless otherwise specified, and containing at least one carbon-carbon triple bond. Representative examples of alkynyl include, but are not limited, to acetylenyl, 1-propynyl, 2-propynyl, 3-butynyl, 2-pentynyl, and 1-butynyl. The term "alkynylene" refers to a divalent alkynyl group, where alkynyl is as defined herein.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring.

An "aralkyl" or "arylalkyl" group comprises an aryl group covalently attached to an alkyl group, either of which independently is optionally substituted. Preferably, the aralkyl group is aryl($C_1$-$C_6$)alkyl, including, without limitation, benzyl, phenethyl, and naphthylmethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane.

The term "halogen" as used herein, means —Cl, —Br, —I or —F.

The terms "haloalkyl", "haloalkenyl" and "haloalkoxy" refer to an alkyl, alkenyl or alkoxy group, as the case may be, which is substituted with one or more halogen atoms.

The term "heteroalkyl" as used herein, refers to an alkyl group in which at least one of carbon atoms has been replaced by O, NR', or S, wherein R' is hydrogen, alkyl, aryl, or aralkyl. The term "heteroalkylene" refers to a divalent heteroalkyl group, where heteroalkyl is as defined herein.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. Representative examples of heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, triazinyl, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, or purinyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocycle is a monocyclic heterocycle fused to either a phenyl, a monocyclic cycloalkyl, a monocyclic cycloalkenyl, a monocyclic heterocycle, or a monocyclic heteroaryl. Representative examples of heterocycle include, but are not limited to, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, 2,3-dihydrobenzofuran-2-yl, and indolinyl.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term, unless stated otherwise.

The term "polyoxyalkylene" refers to moieties formed by polymerizing or copolymerizing two or more of same or different alkylene oxide monomers to provide polymer moieties of desired size and weight, and the polymer moieties can be capped or uncapped. The polymer can be block or random polymer, or both. In general, the alkylene oxide monomers are independently straight or branched chain groups having from 1-8, preferably 2-5, carbon atoms. Where the polymer moiety comprises two or more polyoxyalkylene groups, the individual polyoxyalkylene groups may be connected to each other by linker groups. Examples of suitable linker groups are: —C(O)—, —O—, —O—C(O)O—, —C(O)CH$_2$CH$_2$C(O)—, —S—S—, and —NR$^3$—, where R$^3$ is hydrogen, or C$_1$-C$_6$ alkyl. Non-limiting examples of polyoxyalkylene groups include polyoxyethylene, a straight or branched chain polyoxypropylene, and a straight or branched chain polyoxybutylene. Polyoxyalkylene polymer moieties may have molecular weights of from about 30-3000 Da; any of these moieties may be formed from several shorter, independently-sized units. The units may have molecular weights independently ranging from about 40 (i.e., one repeating unit of a polyethylene glycol), 50, 80, 200, or 500 Da up to about 2000 Da.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

EXAMPLES

Those having skill in the art will recognize that the starting materials and reaction conditions may be varied, the sequence of the reactions altered, and additional steps employed to perform the methods encompassed by the present disclosure, as demonstrated by the following examples. These examples are not to be construed as limiting the disclosure in scope or spirit to the specific procedures and compounds described in them.

Starting materials can be obtained from commercial sources including renewable sources, or prepared by well-established literature methods known to those of ordinary skill in the art. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference in their entirety.

COMPARATIVE EXAMPLE

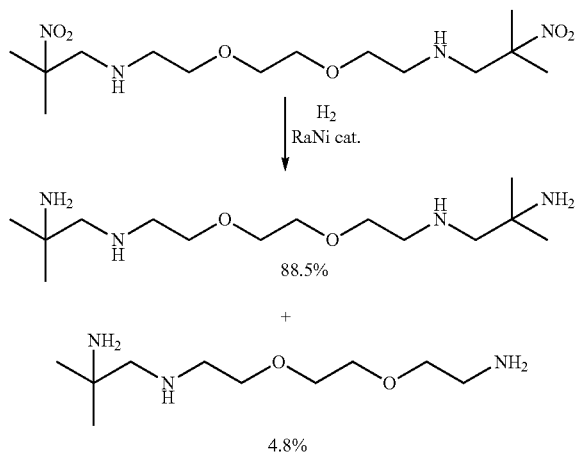

A stainless steel reactor was charged with 53.6 grams (0.153 moles) of N,N'-(2,2'-(ethane-1,2-diylbis(oxy))bis (ethane-2,1-diyl))bis(2-methyl-2-nitropropan-1-amine) (abbreviated as EDBDA-bis-NMP), 57 mL of methanol, and 7.7 grams of BK 111W RaNi catalyst. The reactor was flushed with nitrogen, then pressurized with hydrogen. The reduction was conducted at 750 psig hydrogen at 65° C. The reduction was complete in about 1.5 hours. The reactor mixture was filtered to remove the catalyst; the filtrate was clear and colorless. Retention times were based on GC/MS impurity identification reported in U.S. Patent Publication No. 2012/0196963. The methanol and water were removed from the filtrate by rotary evaporation to give 170.2 grams (88.5%) of $N^1,N^{1'}$-(2,2'-(ethane-1,2-diylbis(oxy))bis(ethane-2,1-diyl))bis(2-methylpropane-1,2-diamine) as a clear, nearly colorless liquid. IR, $^1$H-NMR and $^{13}$C-NMR analyses were consistent with the proposed structure. GC/MS also detected the presence of 4.8% of $N^1$-(2-(2-(2-aminoethoxy) ethoxy)ethyl)-2-methylpropane-1,2-diamine. Also, three additional byproducts were recovered that had retention times (RT) above 20 minutes. These were: $N^1$-(2-(2-(2-(2-amino-2-methylpropylamino)ethoxy)ethoxy)ethyl)-N1,2-dimethylpropane-1,2-diamine (1%), $N^1$-(2-amino-2-methylpropyl)-N1-(2-(2-(2-(2-amino-2-methylpropylamino) ethoxy)ethoxy)ethyl)-2-methylpropane-1,2-diamine (1.6%), and $N^1$-(2-(2-(2-(4,4-dimethylimidazolidin-1-yl)ethoxy) ethoxy)ethyl)-2-methylpropane-1,2-diamine (1.2%).

Example 1

To a 300 mL Parr, stainless steel autoclave, was charged 45 g HPLC grade methanol (MeOH) and 7.7 g R-3111 Ra/Ni catalyst. 53.6 g (0.153 moles) of EDBDA-bis-NMP feed diluted with 6 g of HPLC MeOH was charged to a 150 mL stainless steel cylinder equipped with a feed pump. The autoclave was sealed, pressure purged 3 times with nitrogen ($N_2$), 3 times with hydrogen ($H_2$), and then pressured to and regulated at about 750 psig $H_2$. Agitation begun and was set at 600 rpm. Heating was applied until the autoclave temperature reached 65° C. The EDBDA-bis-NMP/MeOH feed was dosed to the reactor through an Eldex Duros series pump targeting a feed rate of 0.6-0.7 mL/min. After 35 minutes of feed addition (about 25% reaction completion), a reactor sample was taken. The incremental feed was re-started. After an additional 1 hr of EDBDA-bis-NMP/ MeOH feed, 20 mL of methanol was charged to the stainless steel feed tank and allowed to flush into the autoclave. After completion of the MeOH flush, the pump was shut off. Reactor was isolated and held at 65° C. for an additional 10 minutes. The autoclave was cooled to <30° C. and vented. The reaction product was filtered through a glass microfiber filter to remove the catalyst.

Example 2

To a 300 mL Parr, stainless steel autoclave, was charged 45 g HPLC grade methanol and 7.7 g BK-111 W Ra/Ni catalyst. 9.1 g of 2-methyl-2-nitropropan-1-ol (abbreviated as NMP, Angus Chemical Company, Buffalo Grove, Ill.) crystals were dissolved with mixing in 53.6 g (0.153 moles) of EDBDA-bis-NMP, and 6 g of MeOH. The NMP/EDBDA-NMP/MeOH mixture was charged to a 150 mL stainless steel cylinder equipped with a feed pump. The autoclave was sealed, pressure purged 3 times with $N_2$, 3 times with $H_2$, and then pressured to and regulated at about 750 psig $H_2$. Agitation begun and was set at 600 rpm. Heating was applied until the autoclave temperature reached 65° C. The EDBDA-bis-NMP/NMP/MeOH feed was dosed to the reactor through an Eldex Duros series pump targeting a feed rate of 0.6-0.7 mL/min. After about 2.5 hours of feed addition, 20 mL of methanol was charged to the stainless steel feed tank and allowed to flush into the autoclave. After about 30 minutes of MeOH flush, the pump was shut off. Reactor was isolated and held at 65° C. for an additional 10 minutes. The autoclave was cooled to <30° C. and vented. The reaction product was filtered through a glass microfiber filter to remove catalyst.

Example 3

4.2 g Methyl Formcel (Celanese Corp, Irving, Tex.), 6.8 g 2-nitropropane (NiPar S-20, Angus Chemical Company, Buffalo Grove, Ill.) 53.6 g (0.153 moles) EDBDA-bis-NMP, and 0.8 g triethylamine (abbreviated as TEA) were mixed for 15 minutes. The above described mixture was charged to a 150 mL stainless steel cylinder equipped with a feed pump. To a 300 mL Parr, stainless steel autoclave, was charged 45 g MeOH and 7.7 g BK-111 W Ra/Ni catalyst. The autoclave was sealed, pressure purged 3 times with $N_2$, 3 times with $H_2$, and then pressured to and regulated at about 750 psig $H_2$. Agitation begun and was set at 600 rpm. Heating was applied until the autoclave temperature reached 65° C. The EDBDA-bis-NMP/2-NP-Methyl Formcel/TEA/MeOH feed was dosed to the reactor through an Eldex Duros series pump targeting a feed rate of 0.6-0.7 mL/min. After about 2.5 hours of feed addition, 20 mL of methanol was charged to the stainless steel feed tank and allowed to flush into the autoclave. After about 30 minutes of MeOH flush, the pump was shut off. Reactor was isolated and held at 65° C. for an additional 10 minutes. The autoclave was cooled to <30° C. and vented. The reaction product was filtered through a glass microfiber filter to remove catalyst.

Example 4

1.1 g Paraformaldehyde prills, 3.4 g NiPar S-20, and 53.6 g (0.153 moles) EDBDA-bis-NMP were mixed for 24 hours at room temp until the prills were fully dissolved. To the prills/NiPar S-20/EDBDA-bis-NMP mixture, 0.6 g of TEA was added, and the mixing continued for an additional 10 minutes. The above described mixture was charged to a 150 mL stainless steel cylinder equipped with a feed pump. To a 300 mL Parr, stainless steel autoclave, was charged 45 g MeOH and 7.7 g BK-111 W Ra/Ni catalyst. The autoclave was sealed, pressure purged 3 times with $N_2$, 3 times with $H_2$, and then pressured to and regulated at about 750 psig $H_2$. Agitation begun and was set at 600 rpm. Heating was applied until the autoclave temperature reached 65° C. The EDBDA-bis-NMP/2-NP-Paraformaldehyde/TEA/MeOH feed was dosed to the reactor through an Eldex Duros series pump targeting a feed rate of 0.6-0.7 mL/min. After about 2.5 hours of feed addition, 20 mL of MeOH was charged to the stainless steel feed tank and allowed to flush into the autoclave. After about 30 minutes of MeOH flush, the pump was shut off. Reactor was isolated and held at 65° C. for an additional 10 minutes. The autoclave was cooled to <30° C. and vented. The reaction product was filtered through a glass microfiber filter to remove catalyst.

Example 5

2.3 g Paraformaldehyde prills, 6.8 g NiPar S-20, and 53.6 g EDBDA-bis-NMP were mixed for 24 hours at room temp until the prills were fully dissolved. To the prills/NiPer S-20/EDBDA-NMP mixture, 0.6 g of TEA was added, mixing continued for an additional 10 minutes. The above described mixture was charged to a 150 mL stainless steel cylinder equipped with a feed pump. To a 300 mL Parr, stainless steel autoclave, was charged 45 g MeOH and 7.7 g BK-111 W Ra/Ni catalyst. The autoclave was sealed, pressure purged 3 times with $N_2$, 3 times with $H_2$, and then pressured to and regulated at about 750 psig $H_2$. Agitation begun and was set at 600 rpm. Heating was applied until the autoclave temperature reached 65° C. The EDBDA-bis-NMP/2-NP-Paraformaldehyde/TEA/MeOH feed was dosed to the reactor through an Eldex Duros series pump targeting a feed rate of 0.6-0.7 mL/min. After 2.5 hrs of feed addition, 20 mL of methanol was charged to the stainless steel feed tank and allowed to flush into the autoclave. After about 30 minutes of MeOH flush, the pump was shut off. Reactor was isolated and held at 65° C. for an additional 10 minutes. The autoclave was cooled to <30° C. and vented. The reaction product was filtered through a glass microfiber filter to remove catalyst.

Example 6

2.3 g Paraformaldehyde prills, 6.8 g NiPar S-20, and 53.6 g EDBDA-bis-NMP were mixed for 24 hours at room temp until the prills were fully dissolved. To the prills/NiPer S-20/EDBDA-NMP mixture, 0.6 g of TEA was added, mixing continued for an additional 10 minutes. The above described mixture was charged to a 150 mL stainless steel cylinder equipped with a feed pump. To a 300 mL Parr, stainless steel autoclave, was charged 45 g MeOH and 7.7 g BK-111 W Ra/Ni catalyst. The autoclave was sealed, pressure purged 3 times with $N_2$, 3 times with $H_2$, and then pressured to and regulated at about 750 psig $H_2$. Agitation begun and was set at 600 rpm. Heating was applied until the autoclave temperature reached 50° C. The EDBDA-bis-NMP/2-NP-Paraformaldehyde/TEA/MeOH feed was dosed to the reactor through an Eldex Duros series pump targeting a feed rate of 0.6-0.7 mL/min. After 2.5 hrs of feed addition, 20 mL of methanol was charged to the stainless steel feed tank and allowed to flush into the autoclave. After about 30 minutes of MeOH flush, the pump was shut off. Reactor was isolated and held at 50° C. for an additional 10 minutes. The autoclave was cooled to <30° C. and vented. The reaction product was filtered through a glass microfiber filter to remove catalyst.

Example 7

2.3 g Paraformaldehyde prills, 6.8 g NiPar S-20, and 53.6 g EDBDA-bis-NMP were mixed for 24 hours at room temp until the prills were fully dissolved. To the prills/NiPer S-20/EDBDA-NMP mixture, 0.6 g of TEA was added, mixing continued for an additional 10 minutes. The above described mixture was charged to a 150 mL stainless steel cylinder equipped with a feed pump. To a 300 mL Parr, stainless steel autoclave, was charged 45 g MeOH and 7.7 g BK-111 W Ra/Ni catalyst. The autoclave was sealed, pressure purged 3 times with $N_2$, 3 times with $H_2$, and then pressured to and regulated at about 500 psig $H_2$. Agitation begun and was set at 600 rpm. Heating was applied until the autoclave temperature reached 50° C. The EDBDA-bis-NMP/2-NP-Paraformaldehyde/TEA/MeOH feed was dosed to the reactor through an Eldex Duros series pump targeting a feed rate of 0.6-0.7 mL/min. After 2.5 hrs of feed addition, 20 mL of methanol was charged to the stainless steel feed tank and allowed to flush into the autoclave. After about 30 minutes of MeOH flush, the pump was shut off. Reactor was isolated and held at 50° C. for an additional 10 minutes. The autoclave was cooled to <30° C. and vented. The reaction product was filtered through a glass microfiber filter to remove catalyst.

All preparations from Examples 1-7 were submitted for GC analysis. The relative amount of byproduct at approximately 15-minute retention time was the desired component to minimize. The results of these preparations are summarized in Table 1:

TABLE 1

| | | GC Retention Time | | |
|---|---|---|---|---|
| Ex. | Run Type | <10 min | 10.1-20 min | >20 min |
| 1 | 65° C./750 $H_2$/Ra/Ni/MeOH | 0.00 | 6.26 | 93.73 |
| 2 | 65° C./750 $H_2$/Ra/Ni/0.5 mol eq. NMP[1]/MeOH | 11.23 | 6.28 | 82.49 |
| 3 | 65° C./750 $H_2$/Ra/Ni/0.5 mol eq. NP[2] - methyl formcel[3]/0.025 mol eq. TEA[4]/MeOH | 10.30 | 3.37 | 86.33 |
| 4 | 65° C./750 $H_2$/Ra/Ni/0.25 mol eq. NP - paraformaledyde[5]/0.025 mol eq. TEA/MeOH | 4.56 | 1.64 | 93.78 |
| 5 | 65° C./750 $H_2$/Ra/Ni/0.5 mol eq. NP - paraformaledyde/0.025 mol eq. TEA/MeOH | 9.51 | 1.03 | 89.46 |
| 6 | 50° C./750 $H_2$/Ra/Ni/0.5 mol eq. NP - paraformaledyde/0.025 mol eq. TEA/MeOH | 8.01 | 0.91 | 90.85 |
| 7 | 50° C./600 $H_2$/Ra/Ni/0.5 mol eq. NP - paraformaledyde/0.025 mol eq. TEA/MeOH | 9.32 | 1.15 | 89.52 |

[1]NMP = 2-methyl-2-nitropropan-1-ol
[2]NP = 2-nitropropane
[3]Methyl formcel = formaldehyde (55%), MeOH (35%) and $H_2O$ (10%) (Celanese Corp, Irving, TX)
[4]TEA = triethylamine
[5]paraformaldehyde serves as source of formaldehyde Example 1 was used as a baseline. Examples 2, 3, and 5 show that the order of effectiveness, from least effective to most effective, was NMP→NP/methyl formcel→NP/paraformaldehyde. Compared to Example 5, Example 4 reduced the amount of reagents, which increased the level of components at the 10.1-20 min retention time. Using the same reagent amounts from Example 5 to Examples 6 and 7 but decreasing temperature and/or pressure demonstrated the relative robustness of the process over typical manufacturing parameters.

Example 8

NMPD (0.5 Molar Eq.) Hydrogenation Conditions

To a stainless steel autoclave, is charged 45 g HPLC grade tetrhydrofuran and 1.5 g BK-111 W Ra/Ni catalyst. 2.6 g of 2-nitro-2-methyl-1,3-propanediol (NMPD) crystals (ANGUS) are dissolved with mixing in about 0.037 moles of starting nitro compound feed in HPLC tetrahydrofuran (THF), and 6 g of additional THF. The starting material/NMPD/THF mixture is charged to a 150 mL stainless steel cylinder equipped with a feed pump. The autoclave is sealed, pressure purged 3 times with $N_2$, 3 times with $H_2$, and then pressured to and regulated at about 750 psig $H_2$. Agitation begins and sets at 600 rpm. Heating is applied until the autoclave temperature reaches 50° C. The starting material/NMPD/THF feed is dosed to the reactor through an Eldex Duros series pump targeting a feed rate of 0.8-0.9 mL/min. Upon completion of the feed addition (about 1½ hrs), 20 mL of THF is charged to the stainless steel feed tank and allowed to flush into the autoclave. After about 20 minutes of THF flush, the pump is shut off. Reactor is isolated and held at 50° C. for an additional 10 minutes. The autoclave is cooled to <30° C. and vented. The reaction product is filtered through a glass microfiber filter to remove catalyst.

Example 9

NE/Formaldehyde (0.5 Molar Eq.) Hydrogenation Conditions 1.1 g Paraformaldehyde prills, 1.4 g nitroethane (NE), and about 0.037 moles of starting nitro compound feed in HPLC tetrahydrofuran (THF) are mixed for 24 hrs at room temp until the prills are fully dissolved. This mixture is charged to a 150 mL stainless steel cylinder equipped with a feed pump. To a stainless steel autoclave, is charged 45 g THF and 1.5 g BK-111 W Ra/Ni catalyst. The autoclave is sealed, pressure purged 3 times with $N_2$, 3 times with $H_2$, and then pressured to and regulated at about 750 psig $H_2$. Agitation begins and sets at 600 rpm. Heating is applied until the autoclave temperature reaches 50° C. The starting material/NE-paraformaldehyde/THF feed is dosed to the reactor through an Eldex Duros series pump targeting a feed rate of 0.8-0.9 mL/min. After about 1½ hrs of feed addition, 20 mL of THF is charged to the stainless steel feed tank and allowed to flush into the autoclave. After about 20 minute of THF flush, the pump is shut off. Reactor is isolated and held at 50° C. for an additional 10 minutes. The autoclave is cooled to <30° C. and vented. The reaction product is filtered through a glass microfiber filter to remove catalyst.

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

What is claimed is:
1. A method of producing a compound of formula (I):

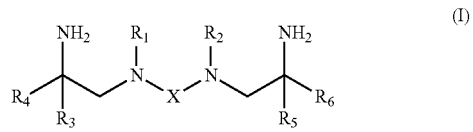

wherein
$R^1$, $R^2$, $R^3$, $R^4$, $R^5$, and $R^6$ are independently selected from H, $C_1$-$C_6$ alkyl, $C_3$-$C_8$ cycloalkyl, $C_3$-$C_8$ cycloalkyl($C_1$-$C_6$ alkyl), aryl, aryl($C_1$-$C_6$ alkyl), heteroaryl, and heteroaryl($C_1$-$C_6$ alkyl); and
X is selected from $C_2$-$C_{20}$ alkylene, $C_2$-$C_{20}$ heteroalkylene, $C_2$-$C_{20}$ alkenylene, $C_2$-$C_{20}$ alkynylene, $C_3$-$C_8$ cycloalkyl, aryl, and —Y—Z—Y—;
wherein each Y independently is $C_1$-$C_{10}$ alkylene, or $C_2$-$C_{10}$ heteroalkylene, and Z is aryl, heteroaryl, or heterocyclyl;
the method comprising reacting a compound of formula (II):

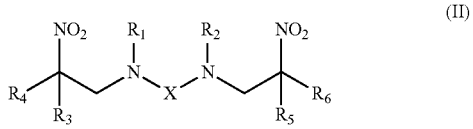

wherein $R^1$, $R^2$, $R^3$, $R^4$, $R^5$, $R^6$, and X are as defined above;
with $H_2$ in a solvent and in the presence of: a) a catalyst, b) at least about 0.1 molar equivalents of a nitro($C_1$-$C_{10}$ alkane) optionally substituted with one or more OH groups, and c) at least about 0.1 molar equivalents of formaldehyde.

2. The method of claim 1, wherein reacting is in the presence of d) a basic amine.

3. The method of claim 2, wherein the basic amine is selected from the group consisting of triethylamine, tri($C_1$-$C_6$ alkyl)amine, tri(hydroxyl $C_1$-$C_6$ alkyl)amine, quinuclidine, morpholine, piperidine, pyridine, imidazole, and alkylimidazole.

4. The method of claim 2, wherein the basic amine is triethylamine and present in about 0.0005 to about 0.2 molar equivalents.

5. The method of claim 1, wherein the catalyst is nickel-based or platinum-based.

6. The method of claim 1, wherein the nitro($C_1$-$C_{10}$ alkane) is 2-nitropropane, 2-methyl-2-nitro-1-propanol, or 2-methyl-2-nitro-1,3-propanediol.

7. The method of claim 1, wherein the nitro($C_1$-$C_{10}$ alkane) is 2-nitropropane or 2-methyl-2-nitro-1-propanol.

8. The method of claim 1, wherein the nitro($C_1$-$C_{10}$ alkane) is present in about 0.1 to about 2 molar equivalents.

9. The method of claim 1, wherein formaldehyde is present in about 0.05 to about 2 molar equivalents.

10. The method of claim 1, wherein $R^1$, $R^2$, $R^3$, $R^4$, $R^5$, and $R^6$ are independently selected from H and $C_1$-$C_6$ alkyl.

11. The method of claim 1, wherein $R^3$, $R^4$, $R^5$, and $R^6$ are independently selected from $C_1$-$C_6$ alkyl.

12. The method of claim 1, wherein $R^1$ and $R^2$ are each H.

13. The method of claim 1, wherein X is $C_2$-$C_{20}$ alkylene or $C_2$-$C_{20}$ heteroalkylene.

14. The method of claim 1, wherein X is hexylene.

15. The method of claim 1, wherein X is a polyoxyalkylene moiety having two or more oxyalkyl groups that are the same or different.

16. The method of claim 1, wherein X is —$(CH_2)_2$—O—$(CH_2)_2$—O—$(CH_2)_2$—.

17. The method of claim 1, wherein the catalyst is Raney nickel.

18. The method of claim 1, wherein the reacting is at a temperature between about 30° C. to about 100° C. and a pressure between about 100 psi to about 1500 psi.

19. The method of claim 1, wherein the compound of formula (I) is:

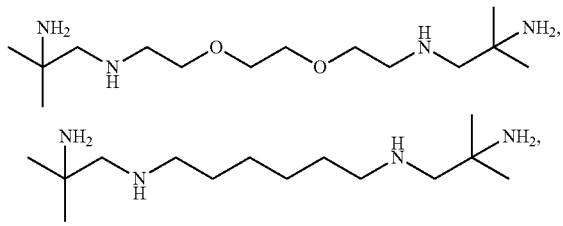

-continued

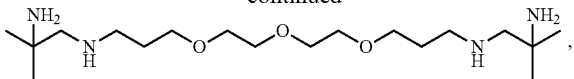

or

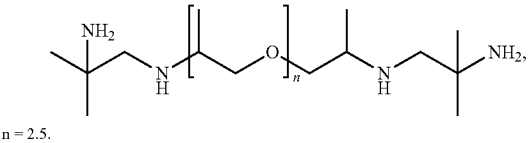

n = 2.5.

20. The method of claim 1, wherein the compound of formula (I) is:

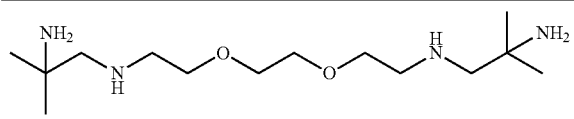

$N^1,N^{1'}$-(2'-(ethane-1,2-diybis(oxyl)bis(ethane-2,1-diyl))bis(2-methylpropane-1,2-diamine), or

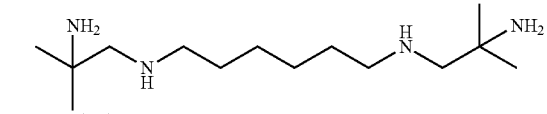 [SMILES: CC(C)(N)CNCCCCCCNCC(C)(C)N]

$N^1,N^{1'}$-(hexane-1,6-diyl)bis(2-methylpropane-1,2-diamine).

* * * * *

UNITED STATES PATENT AND TRADEMARK OFFICE
CERTIFICATE OF CORRECTION

| | | |
|---|---|---|
| PATENT NO. | : 9,434,678 B2 | Page 1 of 1 |
| APPLICATION NO. | : 14/653542 | |
| DATED | : September 6, 2016 | |
| INVENTOR(S) | : David Wayne Moore et al. | |

It is certified that error appears in the above-identified patent and that said Letters Patent is hereby corrected as shown below:

In the Claims

In Claim 20, Column 16, Lines 18-24:

Delete first image caption, "N1,N1'-(2,2'-(ethane-1,2-diybis(oxy))bis(ethane-2,1-diyl))bis(2-methylpropane-1,2-diamine)," and Replace first caption with "N1 ,N1'-(2,2'-(ethane-1,2-diylbis(oxy))bis(ethane-2,1-diyl))bis(2-methylpropane-1,2-diamine)"

Signed and Sealed this
Eleventh Day of July, 2017

Joseph Matal
*Performing the Functions and Duties of the
Under Secretary of Commerce for Intellectual Property and
Director of the United States Patent and Trademark Office*